United States Patent [19]

Hiratsuka

[11] Patent Number: 4,868,131
[45] Date of Patent: Sep. 19, 1989

[54] COMPETITIVE BINDING IMMUNOASSAY PROCESS

[75] Inventor: Nobuo Hiratsuka, Asaka, Japan

[73] Assignee: Fuji Photo Film Co., Ltd., Kanagawa, Japan

[21] Appl. No.: 72,499

[22] Filed: Jul. 13, 1987

[30] Foreign Application Priority Data

Jul. 11, 1986 [JP] Japan ............................. 61-163408

[51] Int. Cl.$^4$ .................... G01N 33/544; G01N 33/50
[52] U.S. Cl. ........................................ 436/528; 435/7; 436/518; 436/523; 436/538; 436/541; 422/56; 422/57
[58] Field of Search ............... 435/4, 7, 805; 436/518, 436/523, 528, 538, 541, 807, 823; 422/56, 57, 101

[56] References Cited

U.S. PATENT DOCUMENTS 4,258,001  3/1981  Pierce et al. ........................ 422/56
4,459,361  7/1984  Gefter ................................. 436/523
4,666,863  5/1987  Edwards et al. ................. 436/518 X

OTHER PUBLICATIONS

Baker et al. in Alternative Immunoassays, 1985, pp. 64–65.

Primary Examiner—Esther M. Kepplinger
Assistant Examiner—Carol A. Spiegel
Attorney, Agent, or Firm—Sughrue, Mion, Zinn, Macpeak & Seas

[57] ABSTRACT

An immunoassay process for quantitative analysis of an analyte antigen (or analyte antibody) in an aqueous liquid sample. In the first step, the analyte antigen (or analyte antibody) is allowed to react with an antibody (or antigen) in competition with a known quantity of a labelled antigen (or labelled antibody), the antibody (or antigen) being carried by water-insoluble microparticles in the immobilized state. In the second step, the reaction mixture is spotted on a top porous layer of an integral multi-layered analysis element which includes the top porous layer, an intermediate detection layer and a bottom water-impermeable and transparent support. The top porous layer permeates aqueous solution and has pores sufficiently small to trap all of the microparticles carrying the antibodies (or antigens) bound to the analyte antigen (or analyte antibody) and bound to the labelled antigen (or labelled antibody). Thus, the free labelled antigen is allowed to pass through the top porous layer and migrate to the detection layer. In the third step, the quantity of the marker labelling to the labelled antigen (or labelled antibody) which has not been bound to the immobilized antibody (immobilized antigen) is determined.

14 Claims, No Drawings

COMPETITIVE BINDING IMMUNOASSAY PROCESS

BACKGROUND OF THE INVENTION

1. Field of the Invention

The present invention relates to an immunoassay process for analyzing bloods or other compositions extracted from living bodies in the clinical examination, and more particularly to a simplified process for immunoassay wherein a dry analytical element (integral multi-layered analysis element) is used to diagnose immunologically the change in disease or the degree of disease or to identify the kind of the disease. The substance contained in blood or other compositions extracted from living bodies and analyzed by the process of this invention will be referred to as "analyte" throughout the specification and appended claims.

2. Related Art Statement

There has been known in the art a variety of immunoassay elements and immunoassay processes in which the so-called antigen-antibody reactions are utilized. The known examination elements include dry analytical elements, such as filter paper impregnated with a reagent, an integral multi-layered analysis element (hereinafter referred to as "multi-layered analysis element" in some portions of this specification) having a reagent layer and a porous spreading layer. However, the accuracies and sensitivities of these known dry-type immunoassay elements are unsatisfactory for practical applications, although they may be used through simple operations.

An example of the known immunoassay process, in which a dry analytical element is used, is a process wherein a slide described in Japanese Patent Laid-Open Publication No. 501144/1983 (WO 83/00391) is used. The slide contains a glass fiber filter sheet which serves as a porous layer. An antibody for the analyte antigen is immobilized on the glass fiber filter sheet. When serum containing the analyte antigen is spotted on the slide, the analyte antigen is bound to the immobilized antibody. An aqueous liquid containing a labelled antigen labelled with a fluorescent marker is then spotted on the sheet so that the labelled antigen is bound to the remaining immobilized antibody which has not been bound to the analyte antigen. The reaction zone of the sheet is rinsed with a rinsing liquid to wash off the excess labelled antigen in a radially outward direction to remove the free labelled antigen from the reaction zone (B/F separation is effected by this rinsing operation). The fluorescent light emitted from the marker in the labelled antigen-antibody complex, which is immobilized by the glass fibers in the reaction zone, is sensed to find the optical density thereof. The thus found datum is compared to a calibration curve to determine the quantity of the analyte antigen contained in the serum. This process is described in "NIPPON RINSHO KENSA JIDOKA GAKKAI-SHI" ("Journal of the Japanese Society of Automation of Clinical Examination"), 10(1), pages 57 to 60 (1985) and in "Clinical Chemistry", 28(9), pages 1894 to 1898 (1985), and applied for practical uses. This known process has a disadvantage in that a rinsing liquid must be supplied precisely to the very center of the reaction zone on the slide to effect B/F separation.

OBJECTS OF THE INVENTION

An object of this invention is to provide an immunoassay process for the quantitative analysis of an analyte at high sensitivity and at high accuracy by combining a simple handling operation of a solution with the use of an integral multi-layered analysis element.

Another object of this invention is to provide an immunoassay process for the quantitative analysis of an analyte without the need of a special operation for B/F separation, wherein competitive immuno-reaction between a labelled immuno-reactant and an unlabelled immuno-reactant takes place in an aqueous solution, followed by a quantitative determination by the use of a dry integral multi-layered analysis element.

SUMMARY OF THE INVENTION

The present invention provides an immunoassay process for quantitative analysis of an analyte antigen in an aqueous liquid sample, wherein an unknown quantity of an analyte antigen is allowed to react with an antibody in competition with a known quantity of a labelled antigen labelled with a marker and the quantity of the marker in the labelled antigen which has not been bound to the antibody is quantitatively determined, comprising:

(a) the step of adding said analyte antigen and said labelled antigen to an aqueous solution containing water-insoluble microparticles on which said antibody is retained in the immobilized state so that competitive antigen-antibody reaction takes place between said immobilized antibody and said analyte antigen and said labelled antigen;

(b) the step of spotting the reaction solution after the completion of said competitive antigen-antibody reaction on an integral multi-layered analysis element including a top porous layer, an intermediate detection layer and a bottom water-impermeable and transparent support, whereby said porous layer traps the labelled antigen bound to said antibody immobilized by said microparticles and allows the free labelled antigen unbound to said antibody to pass therethrough to migrate to said detection layer; and (c) the step of determining the optical density of said detection layer, said optical density being in proportion to the quantity of the marker labelling said labelled antigen migrating to said detection layer.

According to another aspect of this invention, it provides an immunoassay process for quantitative analysis of an analyte antibody in an aqueous liquid sample, wherein an unknown quantity of an analyte antibody is allowed to react with an antigen in competition with a known quantity of a labelled antibody labelled with a marker and the quantity of the marker in the labelled antibody which has not been bound to the antigen is quantitatively determined, comprising:

(a) the step of adding said analyte antibody and said labelled antibody to an aqueous solution containing water-insoluble microparticles on which said antigen is retained in the immobilized state so that competitive antigen-antibody reaction takes place between said immobilized antigen and said analyte antibody and said labelled antibody;

(b) the step of spotting the reaction solution after the completion of said competitive antigen-antibody reaction on an integral multi-layered analysis element including a top porous layer, an intermediate detection layer and a bottom water-impermeable and transparent support, whereby said porous layer traps the labelled antibody bound to said antigen immobilized by said microparticles and allows the free labelled antibody unbound to said antigen to pass therethrough to migrate to said detection layer; and (c) the step of determining the optical density of said detection layer, said optical density being in proportion to the quantity of the marker labelling said labelled antibody migrating to said detection layer.

The colorimetric determination in the step (c) of the process of this invention may be effected, for example, by the following procedure. A predetermined volume of the solution containing the free labelled antigen is spotted on a multi-layered analysis element, followed by incubation at a substantially constant temperature for a certain predetermined period, and then the optical density of the color, fluorescence, turbidity in the visible region or absorption in the ultraviolet region in the analysis element is determined by measuring the reflected light or by measuring the transmitting light from the side of transparent support or from the side of porous layer. Comparing the thus obtained datum with the data on a calibration curve drawn previously, the quantity of the free labelled antigen in the spotted solution is determined. The quantity of the analyte antigen in the aqueous liquid sample may be indirectly determined from the thus determined quantity of the free labelled antigen in the spotted solution. Alternatively, the quantity of the analyte antigen may be determined directly by the use of a calibration curve.

Although the immunoassay process of the invention has been described with reference to a case where an analyte is an antigen, the immunoassay process of the invention can be applied for the analysis of an antibody. In such a case, i.e. when it is desired to determine the quantity of an analyte antibody, similar procedures as described in the preceding paragraph are performed while using a labelled antibody in lieu of the labelled antigen and using similar microparticles carrying thereon an immobilized antigen.

DESCRIPTION OF THE INVENTION

Examples of the labelled antigen or labelled antibody which may be used in this invention include the labelled antigens and labelled antibodies described in the publications listed below.

D. Monroe, "Analytical Chemistry", 56(8), 920A (1984);
Eiji Ishikawa et al., "KOSO-MENEKI SOKUTEIHO" ("Enzyme Immunoassay"), second edition (published by IGAKU SHOIN in 1982);
Fukuko Watanabe, "KENSA-TO-GIJUTSU" ("Examination & Technology"), 9(7), page 583 (1981);
I. Hemmilae, "Clinical Chemistry", 31(3), page 359 (1985); and
Ikuo Johno, "PHARMACIA", 21(2), page 126 (1985).

Labelling materials known in the art and suited for use in this invention include, for example, fluorescent dyes such as FITC (fluorescein isothiocyanate); oxidases such as glucose oxidase (GOD; EC 1.1.3.4) and galactose oxidase (EC 1.1.3.9); hydrolases such as peroxidase (POD; EC 1.11.1.7), alkaline phosphatase (ALP; EC 3.1.3.1) and α-amylase (EC 3.2.1.1); chemiluminescent dyes such as luminol; and oxidizing chemiluminescent enzymes such as luciferase.

The antigen or antibody may be bound to a selected labelling material through any of the conventional processes disclosed, for example, in the following references.

Tadashi Kawai, "RINSHO KENSA GIJUTSU ZENSHO, Vol 4—MENEKI KESSEI KENSA" ("Clinical Examination Technology Series, Vol.-4—Immunoserum Examination"), pages 97 to 102, published by IGAKU SHOIN (1977);
"Biochem. Biophys Res. Commun.", 74, 538 (1977);
"Clinica Chimica Acta", 83, 161 (1978); and Japanese Patent Laid-Open Publication Nos. 79024/1978 (U.S. Pat. No. 4,272,505), 142522/1978 (U.S. Pat. No. 3,998,943), 146295/1976 (U.S. Pat. No. 4,230,797) and 67388/1977 (U.S. Pat. No. 4,230,797)

Specific examples of the labelled antigens and labelled antibodies are GOD bound anti-human immunoglobulin (IgG), ALP bound anti-IgG, α-fetoprotein labelled with POD.

The antigen or antibody may be immobilized by the microparticles and may be bound to a marker by any of the known methods described, for example, in the publications and specifications listed above.

The labelled antigen or labelled antibody is used in the form of an aqueous solution in a pH buffer solution which contains a similar buffer composition as will be described in connection with the buffer solution containing the microparticles for carrying the antigen or antibody in the immobilized state. It is preferred that the solution containing the labelled antigen or labelled antibody is an aqueous solution of a suitable pH buffer selected from the known pH buffer compositions. Particularly when an enzyme is used as the labelling material, it is preferred or even requisite in some cases to adjust and maintain the pH value of the solution within the optimum pH range for the enzyme used. The quantity of the labelled antigen or the labelled antibody should be substantially the same or larger than the quantity of the analyte antigen or the analyte antibody contained in the aqueous liquid sample.

The microparticles for carrying the antigen or antibody in the immobilized state may be solid spherical particles or beads of other shape, and may be made of natural or synthetic organic polymers which do not substantially inhibit the antigen-antibody binding reactions (immuno-reactions), the specific examples of such polymer materials being agarose, gelatin, pururan, cellulose, cellulose acetate, cured polyvinyl alcohol and polystyrene. The fine particles may be in the form of short fibers or microcapsules made of the aforementioned polymer materials. The particle size of the microparticles ranges generally from about 0.1 μm to about 1 mm, preferably from about 0.5 μm to about 100 μm.

It is preferred that the solution containing the microparticles carrying the antigen or antibody is an aqueous solution of a suitable pH buffer selected from the known pH buffer compositions. Particularly when an enzyme is used as the labelling material, it is preferred or even requisite in some cases to adjust and maintain the pH value of the solution, which contains the microparticles carrying the antigen or antibody, within the optimum pH range for the enzyme used. Examples of the pH buffer compositions useful for this purpose are described in the following publications which are hereby incorporated by reference.

"Kagaku Binran, Kiso-hen" (Chemical Handbook, Fundamental Volume), edited by Chemical Society of Japan and published by Maruzen, Tokyo (1966), pages 1312 to 1320;

"Data for Biochemical Research", Second Edition, edited by R. M. C. Dawson et al. and published by Oxford at the Clarendon Press (1969), pages 476 to 508;
"Biochemistry", 5, pages 467–477 (1966); and
"Analytical Biochemistry", 104, pages 300 to 310 (1980).

An embodiment of the integral multi-layered analysis element, which may be used in the practice of the process of this invention, comprises a top porous layer for trapping the microparticles, an intermediate detection layer and a bottom water-impermeable and transparent support. The detection layer is composed of a hydrophilic polymer binder and serves as a water-absorbing layer. The unbound (free) labelled immuno-reactant contained in the aqueous solution and passed to the detection layer is absorbed by the detection layer and the marker labelling thereto is determined by colorimetric determination. An alternative embodiment of the integral multi-layered analysis element comprises a top porous layer for trapping the microparticles, an intermediate coloring reagent layer and a bottom water-impermeable and transparent support. The coloring reagent layer may be composed of a single layer of a hydrophilic polymer binder containing therein a coloring reagent which reacts with the marker labelling to the immuno-reactant, or may be a composite layer including a detection layer composed of a hydrophilic polymer binder layer and a porous layer overlaid on the hydrophilic polymer binder layer.

The porous layer or porous spreading layer may be, for example, a spreading layer made of a woven fabric, such as broad cloth or poplin cloth, as disclosed in Japanese Patent Laid-Open Publication Nos. 164356/1980 (U.S. Pat. No. 4,292,272) and 66359/1982 (GB 2,087,074A); a spreading layer made of a knitted fabric, such as tricot knitted cloth, double-tricot knitted cloth or Milanese stitch knitted cloth, as disclosed in Japanese Patent Laid-Open Publication No. 222769/1985 (EP 0162302A); a spreading layer made of paper containing organic polymer fiber pulp as disclosed in Japanese Patent Laid-Open Publication No. 148250/1982 (corresponding to Chemical Abstract 98:49994q); a non-fibrous isotropically porous spreading layer including a membrane filter (blush polymer layer) or a porous layer containing open cellular micropores composed of polymer microbeads, glass microbeads or diatomaceous earth beads retained by a hydrophilic polymer binder as disclosed in Japanese Patent publication No. 21677/1978 and U.S. Pat. No. 3,992,158; a non-fibrous isotropically porous spreading layer made of a porous layer containing open cellular micropores (three-dimensional lattice structure composed of particles) wherein polymer microbeads are joined together through point-contact joining points by a polymer adhesive which is not swelled by water, as disclosed in Japanese Patent Laid-Open Publication No. 90859/1980 (U.S. Pat. No. 4,258,001); a composite membrane filter (composite blush polymer layer) having a continuous micro-porous structure and having two high polymer micro-porous layers formed by the multi-layer coating method or multi-layer cast coating method as disclosed in Japanese Patent Application No. 232726/1985 (Japanese Patent Laid-Open Publication No. 91543/1987), the two polymer micro-porous layer being intimately joined together across the interfaces thereof to form an integral composite laminate; a composite laminate including a fibrous volume filteration layer prepared through the filter-making process as disclosed in Japanese Patent Laid-Open Publication No. 230063/1985 (EP 159727A) and a fabric layer (made of a woven or knitted cloth), the fibers of the filter layer and the fibers of the fabric layer being entangled at the interfaces between these layers to form an integral composite laminate; a composite laminate including a fibrous volume filtration layer prepared through the filter-making process as disclosed in Japanese Patent Laid-Open Publication No. 230064/1985 (EP 159727A) and a non-fibrous micro-porous layer, such as a membrane filter layer, the fibers of the volume filtration layer anchoring the micropores of the non-fibrous micro-porous layer at the interface between these layers to form an integral composite laminate; and other known glass fiber filter materials. It is generally preferred that the porous layer or the porous spreading layer forms the top layer.

The hydrophilic polymer binder layer (or the water-absorbing or detection layer as referred to in some portions of this specification) is a layer comprising, as a main component, a hydrophilic polymer which absorbs water to be swelled thereby. Water in the aqueous liquid sample permeating through the porous layer or the porous spreading layer onto the interface between the porous layer and the hydrophilic polymer binder layer is absorbed by the latter layer. When the sample used is whole blood, penetration of the aqueous component thereof (i.e. the plasma) onto the reagent layer or detection layer is accelerated by the function of the hydrophilic polymer binder layer. The hydrophilic polymer which may be used in the hydrophilic polymer binder layer has a percentage swelling generally ranging from about 150% to about 2000%, preferably from about 250% to about 1500%, at 30° C. Specific examples of the hydrophilic polymer used in this invention include gelatines, such as a gelatin treated with an acid and a deionized gelatin, gelatine derivatives, such as a phthalated gelatine and a hydroxyacrylate graft gelatin, as disclosed by Japanese Patent Laid-Open Publication Nos. 171864/1984 (EP 119,861A) and 115859/1985 (corresponding to Chemical Abstracts 103:138078h); and agarose, pururan, pururan derivatives, polyacrylamides, polyvinyl alcohol and polyvinyl pyrrolidone as disclosed by Japanese Patent Laid-Open Publication Nos. 171864/1984 (EP 119861A) and 115859/1985. These hydrophilic polymers may be used singly or in combination with one or more other hydrophilic polymers. Generally preferred hydrophilic polymers contained in the hydrophilic polymer binder layer of this invention are gelatine and gelatin derivatives, the other preferable examples thereof being polyacrylamides and polyvinyl alcohol.

The hydrophilic polymer binder layer, in the dry condition, has a thickness generally ranging from about 1 $\mu$m to about 100 $\mu$m, preferably from about 3 $\mu$m to about 30 $\mu$m, and is coated in a coating amount of from about 1 g/m$^2$ to about 100 g/m$^2$, preferably from about 3 g/m$^2$ to about 30 g/m$^2$. The hydrophilic layer binder may contain a known pH buffer, an organic carboxylic acid, an acidic polymer or a basic polymer to have an adjusted pH value at the use (during the analytical operation). The hydrophilic polymer binder layer may be further added with a known mordant or polymer mordant. Although it is preferred that the hydrophilic polymer binder layer is substantially transparent, a small amount of microparticles of titanium dioxide, microparticles of barium sulfate or carbon black may be dispersed therein to control the optical property of the layer, if necessary.

The coloring reagent layer is a water-absorbing and water-permeable layer made of a hydrophilic polymer binder containing therein a reagent composition (coloring reagent composition) which reacts with the marker compound or the marker component of the labelled antibody (or labelled antigen) to induce an optically detectable change, the reagent composition being dispersed substantially uniformly throughout the coloring reagent layer. The optically detectable change means the changes which may be detected by optical measurement, and includes a change in color, coloring (development of a certain color), emittance of a fluoroescent light, a change in absorption wavelength in the ultraviolet range, or occurrence of turbidity.

The hydrophilic polymer binder, which may be used to form the coloring reagent layer, includes hydrophilic polymers which are used in the aforementioned polymer binder layer. The coloring reagent layer, in the dry condition, has a thickness generally ranging from about 3 $\mu$m to about 50 $\mu$m, preferably from about 5 $\mu$m to about 30 $\mu$m, and is coated in a coating amount of from about 3 g/m$^2$ to about 50 g/m$^2$, preferably from about 5 g/m$^2$ to about 30 g/m$^2$. The coloring reagent layer may contain a known pH buffer, an organic carboxylic acid, an acidic polymer or a basic polymer to have an adjusted pH value at the use (during the analytical operation). The coloring reagent layer may be further added with a known mordant or polymer mordant. Although it is preferred that the coloring reagent layer is substantially transparent, a small amount of microparticles of titanium dioxide, microparticles of barium sulfate or carbon black may be dispersed therein to control the optical property of the layer, if necessary.

The coloring reagent layer may be prepared by adding a coloring reagent composition to a porous layer similar to that used as the aforementioned porous layer by the process as disclosed in Japanese Patent Laid-Open Publication No. 4959/1986 (EP 166365A).

A suitable coloring reagent composition may be selected from a variety of known coloring reagent compositions to be contained in the coloring reagent layer.

When an oxidase, such as glucose oxidase or galactose oxidase, or a peroxidase is used as the labelling material, the following are the examples of preferred reagent compositions.

In case where the labelling material is an oxidase (1) A reagent composition containing a peroxidase, a chromogen and a coupler. By the use of such a reagent composition, hydrogen peroxide is generated by the action of the labelling oxidase to act on the chromogen and the coupler so that oxidation coupling of the chromogen and the coupler takes place in the presence of the peroxidase to form a quinoneimine dye.

(2) A reagent composition containing a leuco-dye or an autooxidative chromogen and a peroxidase. By the use of such a reagent composition, hydrogen peroxide is generated by the action of the labelling oxidase to oxidize the leuco-dye or chromogen in the presence of the peroxidase, leading to formation of a coloring dye.

In case where the labelling material is a peroxidase (3) A reagent composition containing an oxidase, a chromogen and a coupler. By the use of such a reagent composition, hydrogen peroxide is generated by the action of the labelling peroxidase to act on the chromogen and the coupler so that oxidation coupling of the chromogen and the coupler takes place in the presence of the peroxidase to form a quinoneimine dye.

(4) A reagent composition containing a leuco-dye or an autooxidative chromogen and an oxidase. By the use of such a reagent composition, hydrogen peroxide is generated by the action of the labelling oxidase to oxidize the leuco-pigment or chromogen in the presence of the labelling peroxidase, leading to formation of a coloring dye.

Examples of the chromogen include 4-aminoantipyrine (also referred to as 4-aminophenazone, i.e. 1-phenyl-2,3-dimethyl-4-amino-3-pyrazolin-5-one) disclosed in "Ann. Clin. Biochem.", 6, 24–27 (1969); and 4-aminoantipyrine analogs including 1-trisubstitutedphenyl-2,3-dimethyl-4-amino-3-pyrazolin-5-ones such as 1-(2,4,6-trichlorophenyl)-2,3-dimethyl-4-amino-3-pyrazolin-5-one disclosed in Japanese Patent Laid-Open Publication No. 54962/1984 (EP 103901A) and 1-(3,5-dichlorophenyl)-2,3-dimethyl-4-amino-3-pyrazolin-5-one, and 1-phenyl-2,3-dimethyl-4-dimethylamino-3-pyrazolin-5-one disclosed in Japanese Patent Publication No. 25840/1980 (U.S. Pat. No. 3,886,045). Amongst these compounds, preferred chromogens are 4-aminoantipyrine, 1-(2,4,6-trichlorophenyl)-2,3-dimethyl-4-amino-3-pyrazolin-5-one and 1-(3,5-dichlorophenyl)-2,3-dimethyl-4-amino-3-pyrazolin-5-one.

Examples of usable couplers are disclosed in "Ann. Clin. Biochem." 6, 24–27 (1969), Japanese Patent Publication Nos. 25840/1980 (U.S. Pat. No. 3,886,045), 45599/1983 ((U.S. Pat. No. 3,983,005) and 18628/1983 (U.S. Pat. No. 4,402,335) and Japanese Patent Laid-open publication Nos. 164356/1980 (U.S. Pat. No. 4,292,272), 124398/1981 (U.S. Pat. No. 4,350,762) and 155852/1981 (U.S. Pat. No. 4,291,121); the specific examples being phenol; phenolsulfonic acids (and alkali metal salts thereof and alkali earth metal salts thereof) such as 2-hydroxy-1-benzenesulfonic acid, 4-hydroxy-1-benzenesulfonic acid, 3,5-dichloro-2-hydroxy-1-benzenesulfonic acid and 2-hydroxy-3-methoxy-1-benzenesulfonic acid; 1-naphthol; 2-naphthol; dihydroxynaphthalenes such as 1,7-dihydroxynaphthalene; naphtholsulfonic acids (and alkali metal salts thereof and alkali earth metal salts thereof) such as 1-hydroxy-4-naphthalenesulfonic acid; and other derivatives of phenol and naphthol. Amongst these compounds, preferable couplers are 1,7-dihydroxynaphthalene, 1-hydroxy-2-naphthalenesulfonic acid (including Na salt, K salt and Li salt thereof), 3,5-dichloro-2-hydroxy-1-benzenesulfonic acid and 2-hydroxy-3-methoxy-1-benzenesulfonic acid (including Na salt, K salt and Li salt thereof).

Examples of usable leuco-dyes are triarylimidazole leuco-dyes, such as 2-(4-hydroxy-3,5-dimethoxyphenyl)-4,5-bis(4-(dimethylamino)phenyl)imidazole disclosed in Japanese Patent Publication No. 5519/1982 (U.S. Pat. No. 4,089,747); and diarylimidazole leuco-dyes such as 2-(3,5-dimethoxy-4-hydroxyphenyl)-4-(4-(dimethylamino)phenyl)-5-phenetylimidazole disclosed in Japanese Patent Laid-Open Publication No. 193352/1984.

Examples of the peroxidase which may be used in this invention are a peroxidase (EC 1.11.1.7) originated from a vegetable or an animal as described in "Rinsho Koso Handbook" (Clinical Enzyme Handbook) edited by Baba, Wada, Kitamura and okuda, Kodansha (1982), "Koso Handbook" (Enzyme Handbook) edited by Maruo and Tamiya, Asakura-shoten (1982), T. E. Barman, "Enzyme Handbook", Springer Verlag (1969) and Japanese Patent Publication Nos. 45599/1981 (U.S. Pat. No. 3,983,055) and 5520/1982 (U.S. Pat. No. 4,211,845); and a peroxidase (EC 1.11.1.7) originated from a microorganism as described in Japanese Patent Publication No. 5035/1983 (Chemical Abstracts 97: 180163q). It is preferred that a non-specific peroxidase originated from a vegetable or a microorganism is used. Examples of preferred peroxidases are horse radish peroxidase, radish peroxidase and peroxidases extracted from microorganisms of *Cochliobolus* and *Curvularia genera.*

A known pH buffer may be contained in the layer containing the peroxidase or the adjacent layer so that the pH value of the layer is maintained within the range of from pH 5.0 to pH 8.0, preferably from pH 6.0 to pH 7.0 during the analyzing operation. The content of peroxidase contained in 1 $m^2$ of the multi-layered element is generally controlled within the range of from about 1,000 U to about 100,000 U, preferably from about 2,000 U to about 60,000 U.

When a hydrolase, such as alkaline phosphatase or α-amylase, is used as the labelling material, the following are the examples of preferred reagent compositions.

In case where the labelling material is an alkaline phosphatase (5) A coloring reagent composition containing an aryl phosphate or a salt thereof, which is an autocoloring substrate, such as p-nitrophenyl phosphate (or a salt thereof, such as Na salt or Tris salt) or p-nitrophenylazonaphthyl phosphate (or a salt thereof, such as bis(2-ethylaminoethanol) salt) disclosed in Japanese Patent Laid-Open Publication No. 110058/1986 (EP 182179A) and Japanese Patent Application No. 111187/1985 (JP Laid-Open Pub. No. 269067/1986).

In case where the labelling material is α-amylase (6) A coloring reagent composition containing a coloring material bound substrate, such as p-nitrophenyl-α-D-maltoheptaoside disclosed in Japanese Patent Laid-Open Publication No. 51892/1979 (U.S. Pat. No. 4,554,631), p-nitrophenyl-α-D-maltopentaoside disclosed in Japanese Patent Laid-Open Publication No. 129997/1983 (U.S. Pat. No. 4,472,499), and a pigment or fluorescent pigment bound starch disclosed in Japanese Patent Laid-Open Publication No. 131089/1978 (U.S. Pat. No. 4,144,306).

The integral multi-layered analysis element may be prepared through the known process described in the patent specifications referred to hereinbefore. It is preferred that the multi-layered analysis element is cut into a square disk having a size of about 15 mm×15 mm to about 30 mm × 30 mm, or a circular disk having substantially the same size, and the disk is contained in a slide frame disclosed in Japanese Patent Publication No. 28331/1982 (U.S. Pat. No. 4,169,751), Japanese Utility Model Publication Nos. 142454/1981 (U.S. Pat. No. 4,387,990) and 32350/1983 and Japanese Patent laid-Open Publication Nos. 63452/1982 and 501144/1983 (WO 83/00391) to form a slide for analysis. For some applications, a continuous tape-shaped multi-layered analysis element may be contained in a cassette or magazine, or a cut piece of the multi-layered analysis element may be contained in a card having an opening at one side.

The immunoassay process of this invention will now be described more specifically by referring to an embodiment thereof wherein the quantity of an antibody contained in an aqueous liquid sample is analyzed by the use of a labelled antibody.

Microparticles on which an antigen for the analyte antibody is carried in the immobilized state are dispersed in a buffer solution having a pH value suited for the expected immuno-reaction to form a dispersion. A predetermined volume of the dispersion is put into a reaction vessel, and added with a predetermined volume of an aqueous liquid sample (e.g. plasma or serum) containing the analyte antibody and further added with a predetermined volume of a buffer solution containing a labelled antibody in an amount of approximately equal to or larger than the estimated maximum quantity of the analyte antibody to obtain a mixed solution. The mixed solution is incubated at a temperature of about 10° C. to about 45° C., preferably from about 20° C. to about 30° C., over a period of from about 3 minutes to about 30 minutes, preferably from about 5 minutes to about 20 minutes, while shaking or stirring the mixed solution for a proper period, whereby competitive immuno-reactions take place between the immobilized antigen and the analyte antibody and the labelled antibody. The incubation is continued until the competitive immuno-reactions are completed. During this incubation operation, a portion of the analyte antibody and a portion of the labelled antibody are bound to the antigen immobilized by the microparticles (there is a case where substantially all of the analyte antibody is bound to the antigen immobilized by the microparticles), and the unbound (free) labelled antibody is left in the buffer solution in the reaction vessel (there is a case where free labelled antibody is substantially zero). Thereafter, a substantially constant volume ranging from about 5 μl to about 100 μl, preferably from about 6 μl to about 70 μl and most preferably a constant volume, of the solution in the reaction vessel is picked up and spotted on the porous spreading layer or the porous layer of the integral multi-layered analysis element, whereby the antibody and labelled antibody bound to the antigen immobilized by the fine particles are trapped by the porous spreading layer or the porous layer, and the free labelled antibody and water acting as a solvent are fed to the coloring reagent layer or the detection layer (this operation corresponds to the B/F separation conducted purposely as a separate operation in the conventional process). The optical density of the color developed in the analysis element is then measured by any of the known methods to determine colorimetrically the quantity of the analyte antibody contained in the aqueous liquid sample.

The quantity of the free labelled antibody retained by the coloring reagent layer or the detection layer of the integral multi-layered analysis element may be determined by any of the known colorimetric determination processes described in the prior patent specifications referred to hereinbefore. In detail, a constant volume of the aqueous liquid sample containing the free labelled antibody is spotted on the spreading layer, and incubated at a substantially constant temperature of from about 20° C. to about 40° C., preferably within a temperature range approximate to about 37° C. (within a temperature range of from about 35° C. to about 40° C.) over a period of from 1 minute to 10 minutes. The optical density of the color, fluoroescence, turbidity or the absorption in the ultraviolet range in the coloring reagent layer of the detection layer of the multi-layered analysis element is measured from the side of the transparent support by a reflection light measurement method (the optical density may be determined by measuring the reflected light from the side of the spreading layer, or may be determined by measuring the transmitted light from the side of support or from the side of the spreading layer). In accordance with the principle of the colorimetric determination method, the quantity of the free labelled antibody in the aqueous liquid sample is determined by comparing the measured datum with the data on a calibration curve drawn previously, and then the quantity of the analyte antibody is indirectly calculated from the thus found quantity of the free labelled antibody. Alternatively, the quantity of the analyte antibody may be determined directly by the use of the calibration curve. A precise datum may be obtained through a simple operation using any of the apparatuses for chemical analysis disclosed, for example, in Japanese Patent Laid-Open Publication Nos. 77746/1981 (U.S. Pat. No. 4,488,810), 21566/1983 (U.S. Pat. No. 4,584,275) and 161867/1983(U.S. Pat. No. 4,424,191).

When the analyte is an antigen, an antibody for the analyte antigen is carried on microparticles in the immobilized state and a labelled antigen is used for the competitive reaction. The other operations are similar to those adopted for the determination of the analyte antibody as described above. Hapten may be analyzed quantitatively through similar operations.

Since an immobilized antigen (an immobilized antibody) is subjected to competitive reaction between an antibody and a labelled antibody (an antigen and a labelled antigen) in an aqueous medium according to the present invention, the competitive reaction takes place more rapidly and more positively than they proceed in a small amount of an aqueous medium retained in a dry integral multi-layered analysis element. Since the colorimetric determination of the labelled antibody (labelled antigen) is conducted using a dry analysis element, the determination can be effected easily within a short time to give an accurate result.

Only by spotting the aqueous liquid sample after the completion of the competitive reaction on the porous layer or the porous spreading layer, the B/F separation which is the most cumbersome and most troublesome operation can be effected automatically without the need of complicated operations, including centrifugal separation or filtration, for B/F separation.

Although the immunoassay process of this invention includes handling of the solution, the process is considerably simplified as compared to the process described in "NIPPON RINSHO KENSA JIDOKA GAKKAI-SHI" ("Journal of the Japanese Society of Automation of Clinical Examination"), 10, pages 57 to 60 (1985) wherein a rinsing solution must be supplied at the center of the reaction zone on a small slide to effect B/F separation. Since such a delicate operation of supplying a rinsing liquid is eliminated in the process of this invention, an accurate quantitative analysis can be effected within a short time by the immunoassay process of this invention.

The present invention will now be described more specifically by referring to the following Examples, given by way of example only.

EXAMPLE (1) Preparation of Integral Multi-layered Analysis Element

An aqueous solution of a coloring reagent composition was coated on a colorless and transparent polyethyleneterephthalate (PET) film having a thickness of 180 $\mu$m and serving as the support, followed by drying, to form a coloring reagent layer having a thickness of about 10 $\mu$m after drying so that the coverage (coated amount) of each of the ingredients in the thus formed coloring reagent layer was set to the amount as described below.

Deionized Gelatin 13 g/m$^2$
Peroxidase 1700 IU/m$^2$
1,7-Dihydroxynaphthalene 330 mg/m$^2$
4-Aminoantipyrine 800 mg/m$^2$
Nonylphenoxypolyethoxyethanol 130 mg/m$^2$
(Containing 10 Oxyethylene Units in Average)

On the other hand, a plain weave cloth made of 100 count thick PET spun yarns was impregnated with an aqueous solution of glucose, followed by drying, so that the cloth contained glucose in an amount of 30 g/m$^2$. In accordance with the method as described in Japanese Patent Laid-Open publication No. 4959/1986 (EP 166365A), the plain weave cloth impregnated with glucose was joined with a cellulose acetate membrane filter having a minimum pore size of 1.2 $\mu$m and a thickness of 140 $\mu$m while using a starch paste, whereby an integral laminate having two intimately joined plies was prepared.

The coloring reagent layer was wetted uniformly with deionized water, and the integral laminate was put on the wet coloring reagent layer so that the plain weave layer was engaged intimately with the coloring reagent layer. A slight compressive force was applied throughout the top side of the integral laminate to prepare an integral multi-layered analysis element.

(2) Immunoassay Operations 1 ml of an aqueous solution of a phosphate buffer having a pH value of 7.0 and containing dispersed polyura microcapsules each having an average particle size of 5 $\mu$m and carrying human immunoglobulin IgG in the immobilized state was put into a test tube, the concentration of the solid components dissolved or dispersed in the solution being 10%. Into the test tube were added 100 $\mu$l of a sample liquid (serum) containing anti-IgG and 100 $\mu$l of an aqueous solution of the phosphate buffer having a pH value of 7.0 and containing dispersed anti-IgG labelled with glucose oxidase (hereinafter referred to as "GOD"). The test tube was shaken for 3 minutes and then allowed to stand still for 2 minutes to allow the anti-IgG and the labelled anti-IgG to react with the immobilized human immunoglobulin in competition with each other. 30 $\mu$l of the dispersion of microcapsules containing unbound (free) GOD labelled anti-IgG was picked up.

30 $\mu$l of the dispersion was spotted on the membrane filter layer of the aforementioned integral multi-layered analysis element, and incubated at 37° C. for 10 minutes. During the period of incubation, the unbound (free) GOD labelled anti-IgG passed through the membrane filter layer to penetrate into the plain weave cloth layer containing glucose, where GOD labelling to the labelled anti-IgG oxidized and decomposed glucose to generate H$_2$O$_2$ which migrated into the coloring reagent layer to form a quinoneimine dye through an oxidation coupling reaction, whereby a color was developed in the coloring reagent layer.

Immediately after the completion of incubation, the optical density of the developed color in the coloring reagent layer was determined while projecting a visible light having a center wavelength of 540 nm from the PET support and measuring the reflected light. It was found that the optical density of the reflected light was in close interrelation with the quantity of the anti-IgG so that the quantity of the anti-IgG could be determined by colorimetric determination.

EXAMPLE 2

(1) Preparation of Integral Multi-layered Analysis Element

An aqueous solution of a coloring reagent composition was coated on a colorless and transparent polyvinylchloride (PVC) film having a thickness of 150 μm and serving as the support, followed by drying, to form a detection layer serving also as a water-absorbing layer and having a thickness of about 15 μm after drying. The coverage (coated amount) of each of the ingredients in the thus formed coloring reagent layer was set to the amount as described below.

Deionized Gelatin Treated with Alkali 20 g/m²
Nonylphenoxypolyethoxyethanol 1000 mg/m²
(Containing 10 Oxyethylne Units in Average)
2-Amino-2-methyl-1-propanol 15 g/m²

On the other hand, a plain weave cloth made of 120 count thick all-cotton spun yarns was impregnated with an aqueous solution of di-Tris p-nitrophenylphospate salt (Tris(hydroxymethyl)aminomethane p-nitrophenylphosphate) in a glycine buffer solution (pH 10.5), followed by drying, so that the cloth contained di-Tris p-nitrophenylphospate salt in an amount of 20 g/m². In accordance with the method as described in Japanese Patent Laid-Open publication No. 4959/1986 (EP 166365A), the plain weave cloth impregnated with the aforementioned reagent composition was joined with a nylon membrane filter having a minimum pore size of 0.6 μm and a thickness of 140 μm while using a starch paste, whereby an integral laminate including two intimately joined plies was prepared.

The detection layer was joined with the plain weave cloth layer of the integral laminate including the two plies to prepare an integral multi-layered analysis element.

(2) Immunoassay Operations 1 ml of an aqueous latex containing dispersed polystyrene microparticles each having an average particle size of 0.8 μm and carrying human immunoglobulin IgG in the immobilized state was put into a test tube, the concentration of the solid components dissolved or dispersed in the solution being 10%. Into the test tube were added 100 μl of a sample liquid (serum) containing anti-IgG and 100 μl of an aqueous solution of the phosphate buffer having a pH value of 7.0 and containing dispersed anti-IgG labelled with alkaline phosphatase (hereinafter referred to as "ALP"). The test tube was shaken for 3 minutes and then allowed to stand still for 2 minutes to allow the anti-IgG and the labelled anti-IgG to react with the immobilized human immunoglobulin in competitive with each other. 50 μl of the dispersion of microparticles containing unbound (free) ALP-labelled anti-IgG was picked up.

50 μl of the dispersion was spotted on the membrane filter layer of the aforementioned integral multi-layered analysis element, and incubated at 37° C. for 7 minutes. During the period of incubation, the unbound (free) AlP-labelled anti-IgG passed through the membrane filter layer (porous layer) to penetrate into the plain weave cloth layer containing the reagent composition, where ALP labelling to the labelled anti-IgG hydrolyzed the p-nitrophenyl phosphate salt to release p-nitrophenol which migrated into the detection layer, whereby a color was developed in the detection layer.

Immediately after the completion of incubation, the optical density of the developed color in the detection layer was determined while projecting a visible light having a center wavelength of 460 nm from the PVC support and measuring the reflected light. It was found that the optical density of the reflected light was in close interrelation with the quantity of the anti-IgG so that the quantity of the anti-IgG could be determined by colorimetric determination.

What is claimed is:

1. An immunoassay process for quantitative analysis of an analyte antigen in an aqueous liquid sample, wherein an unknown quantity of an analyte antigen is allowed to react with an antibody in competition with a known quantity of a labelled antigen labelled with a marker and the quantity of the marker in the labeled antigen which has not been bound to the antibody is quantitatively determined, comprising:
    (a) adding said analyte antigen and said labelled antigen to an aqueous solution comprising water-insoluble microparticles on which said antibody is retained in the immobilized state so that a competitive antigen-antibody reaction takes place between said immobilized antibody and said analyte antigen and said labelled antigen;
    (b) applying an aliquot of the reaction solution after completion of said competitive antigen-antibody reaction on an integral multi-layered analysis element comprising a top porous layer, an intermediate detection layer and a bottom water-impermeable and transparent support, whereby said porous layer traps the labelled antigen bound to said antibody immobilized by said microparticles and allows the free labelled antigen which is not bound to said antibody to pass therethrough to migrate to said detection layer; and
    (c) determining the optical density of said detection layer, said optical density being in proportion to the quantity of the marker labelling to said labelled antigen migrating to said detection layer, thereby to determine the quantity of said analyte antigen contained in said aqueous liquid sample.

2. The immunoassay process according to claim 1, wherein said detection layer comprises a hydrophilic polymer binder which absorbs water and is swelled thereby.

3. An immunoassay process for quantitative analysis of an analyte antigen in an aqueous liquid sample, wherein an unknown quantity of an analyte antigen is allowed to react with an antibody in competition with a known quantity of a labelled antigen labelled with a marker and the quantity of the marker in the labelled antigen which has not been bound to the antibody is quantitatively determined, comprising:
    (a) adding said analyte antigen and said labelled antigen to an aqueous solution containing water-insoluble microparticles on which said antibody is retained in the immobilized state so that a competitive antigen-antibody reaction takes place between said antibody and said analyte antigen and said labelled antigen;
    (b) applying an aliquot of the reaction solution after the completion of said competitive antigen-antibody reaction on an integral multi-layered analysis element comprising a top porous layer, an intermediate color generating reagent layer and a bottom water-impermeable and transparent support, whereby said top porous layer traps the labelled antigen bound to said antibody immobilized by said microparticles and allows the free labelled antigen which is not bound to said antibody to pass therethrough to migrate to said color generating agent layer to develop a color; and (c) measuring the optical density of the color of said color generating reagent layer, the optical density being in proportion to the quantity of the marker labelling to said labelled antigen migrating to said color generating reagent layer, thereby to determine the quantity of said analyte antigen contained in said aqueous liquid sample.

4. The immunoassay process according to claim 3, wherein said color generating reagent layer comprises a hydrophilic polymer binder and a color generating reagent.

5. The immunoassay process according to claim 3, wherein said color generating reagent layer is a porous layer comprising a color generating reagent, and wherein a detection layer comprising a hydrophilic polymer binder is interposed between said color generating reagent layer and said support.

6. An immunoassay process for quantitative analysis of an analyte antibody in an aqueous liquid sample, wherein an unknown quantity of an analyte antibody is allowed to react with an antigen in competition with a known quantity of a labelled antibody labelled with a marker and the quantity of the marker in the labelled antibody which has not been bound to the antigen is quantitatively determined, comprising:

(a) adding said analyte antibody and said labelled antibody to an aqueous solution containing water-insoluble microparticles on which said antigen is retained in the immobilized state so that a competitive antigen-antibody reaction takes place between said immobilized antigen and said analyte antibody and said labelled antibody;

(b) applying an aliquot of the reaction solution after the completion of said competitive antigen-antibody reaction on an integral multi-layered analysis element comprising a top porous layer, an intermediate detection layer and a bottom water-impermeable and transparent support, whereby said porous layer traps the labelled antibody bound to said antigen immobilized by said microparticles and allows the free labelled antibody which is not bound to said antigen to pass therethrough to migrate to said detection layer; and (c) determining the optical density of said detection layer, said optical density being in proportion to the quantity of the marker labelling to said labelled antibody migrating to said detection layer, thereby to determine the quantity of said analyte antibody contained in said aqueous liquid sample.

7. The immunoassay process according to claim 6, wherein said detection layer comprises a hydrophilic polymer binder which absorbs water and is swelled thereby.

8. An immunoassay process for quantitative analysis of an analyte antibody in an aqueous liquid sample, wherein an unknown quantity of an analyte antibody is allowed to react with an antigen in competition with a known quantity of a labelled antibody labelled with a marker and the quantity of the marker in the labelled antibody which has not been bound to the antigen is quantitatively determined, comprising:

(a) adding said analyte antibody and said labelled antibody to an aqueous solution containing water-insoluble microparticles on which said antigen is retained in the immobilized state so that a competitive antigen-antibody reaction takes place between said immobilized antigen and said analyte antibody and said labelled antibody;

(b) applying an aliquot of the reaction solution after the completion of said competitive antigen-antibody reaction on an integral multi-layered analysis element comprising a top porous layer, an intermediate color generating reagent layer and a bottom water-impermeable and transparent support, whereby said top porous layer traps the labelled antibody bound to said antigen immobilized by said microparticles and allows the free labeled antibody which is not bound to said antigen to pass therethrough to migrate to said color generating reagent layer to develop a color; and (c) measuring the optical density of the color of said color generating reagent layer, the optical density being in proportion to the quantity of the marker labelling to said labelled antibody migrating to said color generating reagent layer thereby to determine the quantity of said analyte antibody contained in said aqueous liquid sample.

9. The immunoassay process according to claim 8, wherein said color generating reagent layer comprises a hydrophilic polymer binder and a color generating reagent.

10. The immunoassay process according to claim 8, wherein said color generating reagent layer is a porous layer comprising a color generating reagent, and wherein a detection layer comprising a hydrophilic polymer binder is interposed between said color generating reagent layer and said support.

11. The immunoassay process according to claim 1, wherein the microparticles have a particle size of about 0.1 $\mu$m to about 0.1 mm.

12. The immunoassay process according to claim 3, wherein the microparticles have a particle size of about 0.1 $\mu$m to about 0.1 mm.

13. The immunoassay process according to claim 6, wherein the microparticles have a particle size of about 0.1 $\mu$m to about 0.1 mm.

14. The immunoassay process according to claim 8, wherein the microparticles have a particle size of about 0.1 $\mu$m to about 0.1 mm.

* * * * *